United States Patent [19]

Valenta

[11] Plant 4,885

[45] Sep. 7, 1982

[54] ALMOND TREE

[75] Inventor: Frank E. Valenta, Delhi, Calif.

[73] Assignee: Thomas Francis Valenta, Atwater, Calif. ; a part interest

[21] Appl. No.: 227,461

[22] Filed: Jan. 22, 1981

[51] Int. Cl.[3] ..... A01H 5/03

[52] U.S. Cl. ..... Plt./30

[58] Field of Search ..... Plt./30

*Primary Examiner*—Robert E. Bagwill

*Attorney, Agent, or Firm*—Roger B. Webster

[57] ABSTRACT

An almond tree which is large, spreading, dense, and vigorous; abundantly foliated with small, lanceolate, acutely pointed leaves having a finely serrate margin, and small, green, alternate, globose glands; blooms white and very heavily; and is a regular and very heavy bearer of small, well-sealed nuts having medium size, sweet kernels of very good quality.

1 Drawing Figure

BACKGROUND OF THE VARIETY

Classification of the Variety

The present new and distinct variety of almond tree is embraced by Class 30, Plants, of the U.S. Patent Office Manual of Classification.

Prior Varieties

Among the existent varieties of almond tree which are known to me, and mentioned herein, are Thompson (unpatented), Nonpareil (unpatented), and Merced (U.S. Plant Pat. No. 1,730).

ORIGIN OF THE VARIETY

The present variety of almond tree was discovered by me growing, as a chance seedling, adjacent a building on my premises located near Delhi, Merced County, Calif.; such seedling having been permitted to grow to maturity initially for shade. However, in maturity, and when the tree bore crops, I recognized and confirmed—upon careful and continuing observation—that the tree and its nuts had certain novel characteristics. I, therefore, determined to asexually reproduce the tree as a variety having merit for possible commercial growing.

ASEXUAL REPRODUCTION OF THE VARIETY

The present variety of almond tree was successfully asexually reproduced by me, by spring budding, on my premises located as aforesaid, and—in maturity—the asexual reproductions ran true, in all respects, to the original tree.

SUMMARY OF THE VARIETY

The present variety of almond tree is large, spreading, dense, and vigorous; abundantly foliated with small, lanceolate, acutely pointed leaves having a finely serrate margin, and small, green, alternate, globose glands; blooms white and very heavily; and is a regular and very heavy bearer of small, well-sealed nuts having medium size, sweet kernels of very good quality.

The present variety of almond tree is further characterized by general resemblance to the Thompson, but blooms approximately two weeks earlier and hence is an excellent pollinator for the Nonpareil; the present variety blooming about two days after the onset of the Nonpareil bloom.

The present variety of almond tree is still further characterized by a harvest period after the Thompson and Nonpareil and approximately with the Merced.

BRIEF DESCRIPTION OF THE DRAWING

The drawing is an illustration, by photographic reproduction in color, of a twig with leaves and nuts, and, separately, nuts in hull, nuts out of hull, and kernels.

DESCRIPTION OF THE VARIETY

The botanical details of this new and distinct variety of almond tree—with color definitions (except those in common color terms) referenced to Maerz and Paul Dictionary of Color (Second Edition)—are as follows:

Tree:
- *Density.*—Dense.
- *Size.*—Large.
- *Vigor.*—Vigorous.

Trunk:
- *Form.*—Medium.
- *Texture.*—Shaggy.

Branches:
- *Form.*—Medium.
- *Texture.*—Medium.
- *Lenticels.*—Medium number. Medium size.
- *Branching habit.*—Spreading.
- *Color.*—New wood: green (22-K-5). Mature wood: dull gray (15-C-6).

Foliage:
- *Quantity.*—Abundant.

Leaves:
- *Size.*—Small. Length range — 60-65 mm. Width range — 13-17 mm.
- *Shape.*—Lanceolate. Acutely pointed.
- *Thickness.*—Medium.
- *Texture.*—Smooth.
- *Margin.*—Finely serrate.
- *Petiole.*—Long. Medium thickness.
- *Glands.*—Average number — 3. Alternate. Small. Globose. Green. Positioned on petiole adjacent leaf blade.
- *Color.*—Top side — medium green (23-H-7). Under side — lighter green (23-E-6).

Bloom:
- *Amount of bloom.*—Very heavy.
- *Color.*—White.

Blooming period.—Medium. Two weeks before Thompson, and two days after Nonpareil.

Crop:

*Bearing.*—Regular bearer.

*Productivity.*—Very heavy.

*Distribution of nuts on tree.*—On short spurs. Well distributed.

*Harvest period.*—Late. With Merced.

*Tenacity.*—Hangs well on tree. Medium to harvest. Easy to hull.

Hull:

*Outer surface.*—Smooth.

*Form.*—Regular.

*Thickness.*—Thin.

*Flesh.*—Tough.

*Suture.*—Ridged.

*Color.*—Light olive green (13-L-2) when fresh. Gray-green (14-B-2) when dry.

*Dehiscence.*—Opens partially.

*Splitting.*—Along suture.

Nut:

*Size.*—Medium. Length range — 30–35 mm. Width range — 18–20 mm. Thickness range — 13–17 mm. Average weight — 2.1 grams per nut.

*Form.*—Length/width: ovate. Width/thickness: plump.

*Shell.*—Semi-hard. Thick. Smooth. Outer shell: hard to crumbling. Inner shell: hard. Well sealed.

*Color.*—Light desert tan (12-I-7).

*Pits.*—Small. Numerous. Deep. Round.

*Base.*—Dorsally oblique.

*Stem scar.*—Large. Obtuse.

*Apex.*—Acuminate. Tip recurved.

*Wings.*—Narrow. Thin. Even.

*Inner surface.*—Dark colored.

*Ventral streak.*—Dark. Long.

*Percentage of kernel to nut.*—56%.

Kernel:

*Size.*—Medium. Length range — 20–22 mm. Width range — 10–12 mm. Thickness range — 7–9 mm. Average weight — 1.15 gram per nut.

*Form.*—Length/width: ovate. Width/thickness: plump.

*Base.*—Dorsally oblique.

*Stem scar.*—Large. Obtuse.

*Apex.*—Acute. Sharp. Tip recurved.

*Texture.*—Smooth. Furrowed.

*Pellicle.*—Thin.

*Pubescence.*—Smooth. Veined.

*Color.*—Medium light brown (13-H-10).

*Number of doubles.*—Medium.

*Defective kernels.*—Substantially absent.

*Flavor.*—Sweet. Normal.

*Quality.*—Very good.

Susceptibility or resistance to insects and diseases: Average — no specific acute problems noted.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, particularly characterized by a blooming period approximately two weeks earlier than the Thompson and about two days after the Nonpareil, and by a harvest period after the Thompson and Nonpareil and approximately with the Merced.

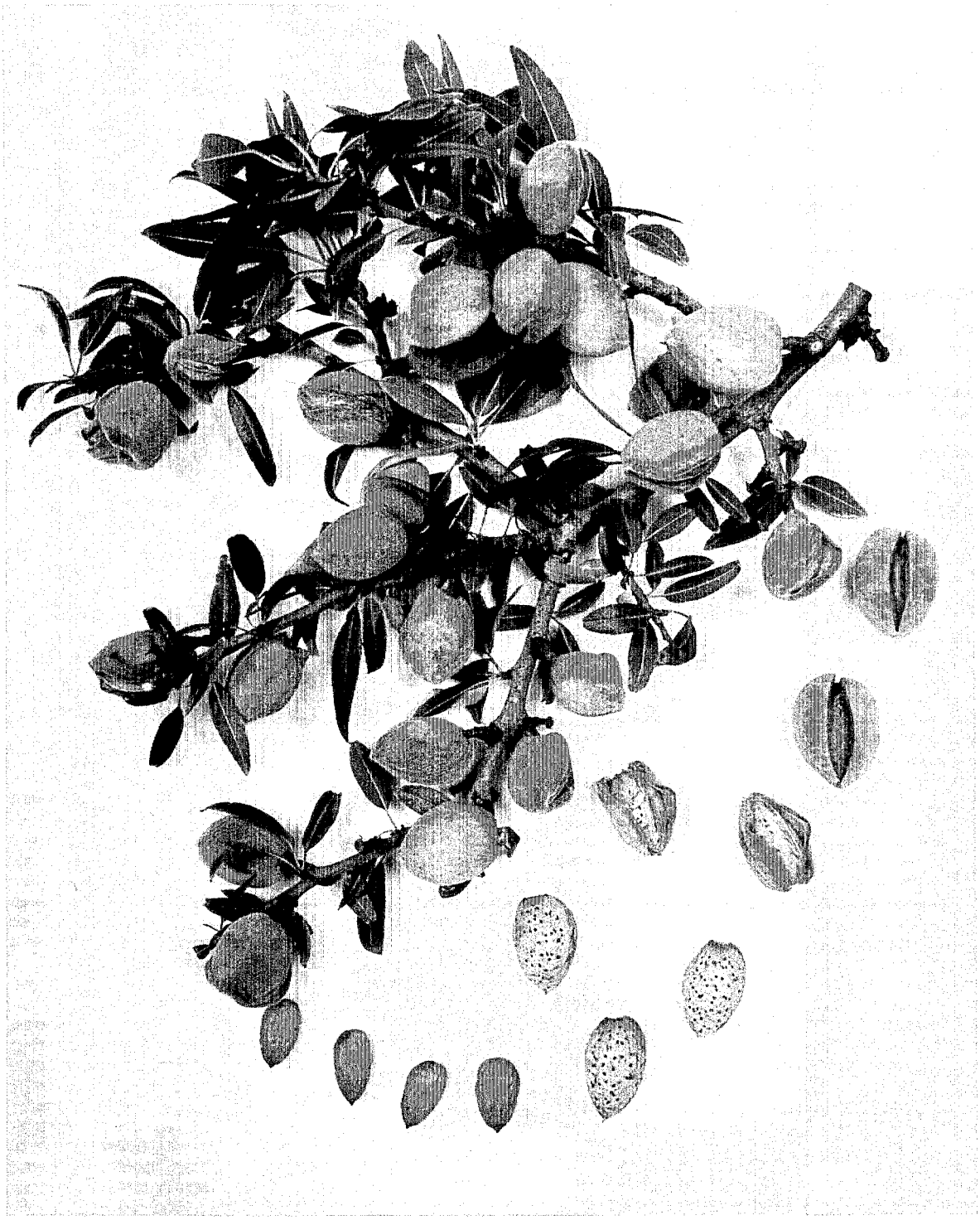

* * * * *